United States Patent
Soulet De Brugiere et al.

(10) Patent No.: US 10,695,528 B2
(45) Date of Patent: Jun. 30, 2020

(54) DEVICE AND METHOD FOR STIMULATING SLOW BRAIN WAVES

(71) Applicant: RYTHM, Paris (FR)

(72) Inventors: Quentin Soulet De Brugiere, Pyla sur Mer (FR); Hugo Mercier, Chilly Mazarin (FR); Mathieu Galtier, Antibes (FR)

(73) Assignee: DREEM, Paris (FR)

( * ) Notice: Subject to any disclaimer, the term of this patent is extended or adjusted under 35 U.S.C. 154(b) by 331 days.

(21) Appl. No.: 15/531,323

(22) PCT Filed: Nov. 27, 2015

(86) PCT No.: PCT/EP2015/077959
§ 371 (c)(1),
(2) Date: May 26, 2017

(87) PCT Pub. No.: WO2016/083598
PCT Pub. Date: Jun. 2, 2016

(65) Prior Publication Data
US 2017/0340855 A1   Nov. 30, 2017

(30) Foreign Application Priority Data
Nov. 27, 2014   (FR) ..................................... 14 61538

(51) Int. Cl.
*A61M 21/02*   (2006.01)
*A61B 5/00*   (2006.01)
(Continued)

(52) U.S. Cl.
CPC ........... *A61M 21/02* (2013.01); *A61B 5/4812* (2013.01); *A61B 5/6814* (2013.01); *A61B 5/0478* (2013.01);
(Continued)

(58) Field of Classification Search
CPC . A61B 5/04845; A61B 5/6814; A61B 5/4836; A61B 5/0496; A61B 5/0488;
(Continued)

(56) References Cited

U.S. PATENT DOCUMENTS 3,884,218 A     5/1975   Monroe
4,883,067 A *  11/1989  Knispel ................ A61B 5/0482
                                                            600/545
(Continued)

FOREIGN PATENT DOCUMENTS

EP         2 348 969 A     8/2011
WO      2006/101571 A2    9/2006
(Continued)

OTHER PUBLICATIONS

Hong-Viet V Ngo et al. "Auditory Closed-Loop Stimulation of the Sleep Slow Oscillation Enhances Memory" Neuron 78, 545-553, May 8, 2013 ᵃ2013 Elsevier Inc. pp. 545-553.
(Continued)

*Primary Examiner* — Navin Natnithithadha
*Assistant Examiner* — Sunita Reddy
(74) *Attorney, Agent, or Firm* — Young & Thompson

(57) ABSTRACT

The invention relates to a self-contained device (1) for stimulating slow brain waves, capable of being worn by a person (P), in particular during a period of time when said person is sleeping. The device (1) comprises a supporting element (2), capable of surrounding the head of a person, and on which electrodes (3) are mounted in contact with the person in order to acquire a measurement signal that represents a physiological electrical signal of the person; an acoustic transducer (4) for emitting an acoustic signal (A) stimulating the inner ear of the person; and on-board conditioning and control electronics (5) for, in flexible real time, receiving the measurement signal and controlling the emis-
(Continued)

sion of an acoustic signal (A) synchronised with a predefined slow brain wave time pattern.

31 Claims, 3 Drawing Sheets

(51) Int. Cl.
    *A61B 5/0484*     (2006.01)
    *A61M 21/00*     (2006.01)
    *A61B 5/0496*     (2006.01)
    *A61B 5/0488*     (2006.01)
    *A61B 5/0478*     (2006.01)

(52) U.S. Cl.
    CPC .......... *A61B 5/0488* (2013.01); *A61B 5/0496* (2013.01); *A61B 5/04845* (2013.01); *A61B 5/4836* (2013.01); *A61M 2021/0005* (2013.01); *A61M 2021/0027* (2013.01); *A61M 2205/3553* (2013.01); *A61M 2205/3584* (2013.01); *A61M 2205/3592* (2013.01); *A61M 2205/52* (2013.01); *A61M 2205/8206* (2013.01); *A61M 2209/088* (2013.01); *A61M 2210/06* (2013.01); *A61M 2230/04* (2013.01); *A61M 2230/10* (2013.01); *A61M 2230/14* (2013.01); *A61M 2230/60* (2013.01)

(58) Field of Classification Search
    CPC .............. A61B 5/4812; A61B 5/0478; A61M 2210/06; A61M 21/02; A61M 2021/0027; A61M 2205/3553; A61M 2205/3584; A61M 2205/3592; A61M 2205/52; A61M 2205/8206; A61M 2209/088; A61M 2230/04; A61M 2230/10; A61M 2230/14; A61M 2230/60; A61M 2021/0005; A61M 2230/005
    USPC ....................................... 600/26–28
    See application file for complete search history.

(56) References Cited

U.S. PATENT DOCUMENTS

| | | | | |
|---|---|---|---|---|
| 5,365,939 A * | 11/1994 | Ochs | ................. | A61B 5/0482 600/544 |
| 5,409,445 A * | 4/1995 | Rubins | ................. | A61M 21/00 600/27 |
| 5,740,812 A * | 4/1998 | Cowan | ................. | A61B 5/0482 600/545 |
| 5,853,005 A * | 12/1998 | Scanlon | ................. | A61B 5/113 600/459 |
| 6,385,486 B1 * | 5/2002 | John | ................. | A61B 5/0002 600/544 |
| 6,402,520 B1 * | 6/2002 | Freer | ................. | A61B 5/0482 434/236 |
| 6,488,617 B1 * | 12/2002 | Katz | ................. | A61B 5/0482 600/26 |
| 6,574,513 B1 * | 6/2003 | Collura | ................. | A61B 5/0478 600/153 |
| 7,749,154 B2 | 7/2010 | Cornel | | |
| 8,029,431 B2 | 10/2011 | Tononi | | |
| 8,382,484 B2 | 2/2013 | Wetmore et al. | | |
| 2005/0283039 A1 | 12/2005 | Cornel | | |
| 2006/0116597 A1 * | 6/2006 | Vesely | ................. | A61B 5/04008 600/545 |
| 2007/0282216 A1 | 12/2007 | Vesely et al. | | |
| 2008/0013777 A1 * | 1/2008 | Park | ................. | A61B 5/0059 381/384 |
| 2008/0304691 A1 * | 12/2008 | Lai | ................. | H04R 5/0335 381/386 |
| 2010/0198318 A1 * | 8/2010 | Rogers | ................. | A61F 7/007 607/99 |
| 2010/0217099 A1 * | 8/2010 | LeBoeuf | ................. | A61B 5/00 600/301 |
| 2011/0009921 A1 * | 1/2011 | Tass | ................. | A61B 5/486 607/45 |
| 2011/0105938 A1 * | 5/2011 | Hardt | ................. | A61B 5/0482 600/544 |
| 2012/0271377 A1 * | 10/2012 | Hagedorn | ................. | A61B 5/0482 607/45 |
| 2013/0035578 A1 | 2/2013 | Chiu et al. | | |
| 2013/0245422 A1 * | 9/2013 | D'arcy | ................. | A61B 5/0484 600/409 |
| 2013/0314303 A1 * | 11/2013 | Osterhout | ................. | G06F 3/005 345/8 |
| 2014/0342338 A1 * | 11/2014 | Imran | ................. | G09B 5/04 434/319 |
| 2015/0051663 A1 * | 2/2015 | Hagedorn | ................. | A61N 2/006 607/45 |
| 2015/0313539 A1 * | 11/2015 | Connor | ................. | A61B 5/7285 600/544 |
| 2017/0296121 A1 * | 10/2017 | Dar | ................. | A61B 5/0478 |

FOREIGN PATENT DOCUMENTS

| | | |
|---|---|---|
| WO | 2009/065076 A1 | 5/2009 |
| WO | 2010042615 A2 | 4/2010 |
| WO | 2011055304 A1 | 5/2011 |
| WO | 2012097872 A1 | 7/2012 |
| WO | 2012108736 A2 | 8/2012 |
| WO | 2014/152887 A1 | 9/2014 |

OTHER PUBLICATIONS

Lisa Marshall et al. "Boosting slow oscillations during sleep potentiates memory" vol. 444130 Nov. 2006, pp. 610-613.
Marcello Massimini et al. "The Sleep Slow Oscillation as a Traveling Wave", The Journal of Neuroscience, Aug. 4, 2004 • 24(31):6862-6870.
FR Search Report, dated Aug. 10, 2015, from corresponding FR application.
International Search Report, dated Feb. 5, 2016, from corresponding PCT application.

* cited by examiner

DEVICE AND METHOD FOR STIMULATING SLOW BRAIN WAVES

FIELD OF THE INVENTION

The invention relates in general to the field of controlling brain activity during sleep, and in particular to stimulating slow brain waves in order to reinforce the beneficial effects of a person's sleep.

The invention therefore firstly relates to a device for stimulating slow brain waves, and secondly to a method for stimulating slow brain waves of a person wherein the person wears such a device.

BACKGROUND OF THE INVENTION

During a person's sleep period, many crucial biological processes take place such as development of the immune defenses, cell regeneration, or memory consolidation.

A sleep deficit or poor quality sleep are therefore now recognized as sources of memory disorders and as important factors in the development or aggravation of serious diseases such as Alzheimer's, Parkinson's, hypertension, or obesity.

It has been observed that these beneficial biological mechanisms associated with sleep are associated with a specific brain activity with waves of specific frequency: the slow brain waves.

In modern societies, stress and productivity constraints lead to poor and shortened sleep, particularly for the sleep stages in which the beneficial biological mechanisms mentioned above occur. This has adverse effects in the short term (fatigue, memory, concentration) and long term (increased risk of onset of chronic diseases).

There is thus a general need to enhance the beneficial effects of a person's sleep, particularly when the duration and quality of sleep are subjected to strong external stresses.

For that purpose there are known devices for stimulating the brain, in particular during a person's deep sleep stages, which seek to promote deep sleep.

For example, document U.S. Pat. No. 8,029,431 describes a system applying non-invasive stimulation to a person's brain during a deep sleep stage. The system comprises a central processing unit receiving the signals measured by an electrode panel in order to capture an electroencephalogram of a person and control a transcranial magnetic stimulation device so as to stimulate the person's brain periodically at a predefined frequency when in deep sleep, in order to enhance deep sleep.

Such a device has disadvantages: a transcranial stimulation device is bulky and little suited for daily use since it involves a hinged stand on which is hung a coil powered by a generator. Furthermore, such a device must be properly positioned relative to the target areas of the brain, which is difficult to achieve throughout a night's sleep, especially when the person moves about in the bed, and therefore implies reliance on a robotic arm controlled by computer, further restricting the applicability of the solution to daily use. Moreover, a given periodic stimulation is not adapted for everyone due to brain wave variability from one individual to another, and the use of such a device therefore requires the presence of medical personnel trained in determining and adjusting the stimulation frequency for the user, which further complicates the adoption of such a device in daily use and its ease of use.

There is therefore a need for a device for stimulating slow brain waves that is easy to use, accessible to non-medically trained personnel, and compact and comfortable so that it can be used in an everyday context, which significantly enhances the beneficial effects of a person's sleep, which improves where appropriate the stability and duration of sleep stages, which is easily adaptable to the user so that it can be used by a variety of people without complex modifications, and which is simple and inexpensive to manufacture so as to guarantee its accessibility to the general public.

OBJECTS OF THE INVENTION

To this end, the first object of the invention is a self-contained device for stimulating slow brain waves, adapted to be worn by a person, in particular during a sleep period of said person, the device comprising a supporting member, adapted to surround the person's head at least partially so as to be held thereon, on which are mounted:

a plurality of electrodes adapted to be in contact with the person in order to capture at least one measurement signal that represents a physiological electrical signal of said person, at least one acoustic transducer adapted to emit an acoustic signal stimulating an inner ear of said person, and embedded conditioning and control electronics adapted to, in soft real-time, receive the measurement signal from the plurality of electrodes and control the emission by the acoustic transducer of an acoustic signal synchronized with a predefined slow brain wave temporal pattern.

In preferred embodiments of the invention, one or more of the following arrangements may possibly be used:

for controlling the emission by the acoustic transducer of an acoustic signal synchronized with a predefined slow brain wave temporal pattern, the embedded conditioning and control electronics are adapted to:

determine, from the measurement signal, a slow brain wave temporal waveform, determine, from said slow brain wave temporal waveform, at least one temporal moment of synchronization between the predefined slow brain wave temporal pattern and a predefined temporal pattern of the acoustic signal, and control the acoustic transducer so that the predefined temporal pattern of the acoustic signal is emitted at said temporal moment of synchronization;

the means for determining a slow brain wave temporal waveform from the measurement signal, of the embedded conditioning and control electronics, comprise a phase-locked loop;

the phase-locked loop is adapted to adjust an instantaneous phase of the temporal waveform according to an instantaneous phase of the measurement signal;

the phase-locked loop comprises means for determining an instantaneous phase difference between the temporal waveform and the measurement signal, in particular a low-pass filter applied to a product between the temporal waveform and the measurement signal;

the predefined slow brain wave temporal pattern has a predefined range of instantaneous phase values of the temporal waveform and/or a predefined range of absolute values of the measurement signal amplitude;

the acoustic transducer is a speaker stimulating the inner ear of the person via an ear canal, or an osteophonic device stimulating the inner ear of the person via bone conduction;

the embedded conditioning and control electronics receive the measurement signal from the plurality of electrodes and control the acoustic transducer by means of wired connections;

the device further comprises a memory, mounted on the supporting member, controlled by the embedded conditioning and control electronics and adapted to store the measurement signals, preferably a memory adapted to store the measurement signals for several hours, more preferably at least eight hours;

the memory is capable of storing an average slow brain wave frequency of the person;

the device further comprises a module for communicating with an external server, mounted on the supporting member, controlled by the embedded conditioning and control electronics, and adapted to transfer the stored measurement signals to the external server, in particular after a sleep period of said person;

the device is self-contained and adapted to implement a slow brain wave stimulation operation without communicating with an external server, in particular without communicating with an external server for several minutes, preferably several hours, more preferably at least eight hours;

the device comprises a battery mounted on the supporting member and adapted to supply power to the plurality of electrodes, the acoustic transducer, and the embedded conditioning and control electronics, preferably over several hours without recharging the battery, more preferably at least eight hours;

the slow brain wave has a frequency less than 5 Hz and greater than 0.3 Hz;

the acoustic signal is an intermittent signal and a duration of the acoustic signal is less than a period of a slow brain wave, preferably less than a few seconds, more preferably less than one second;

the acoustic signal is a continuous signal and a duration of the acoustic signal is greater than a period of a slow brain wave;

the device comprises a first acoustic transducer and a second acoustic transducer respectively adapted to emit acoustic signals respectively stimulating a right inner ear and a left inner ear of the person, and the acoustic signals emitted by the first and second acoustic transducers are binaural acoustic signals;

the predefined slow brain wave temporal pattern corresponds to a local temporal peak of a slow brain wave, a local temporal valley of a slow brain wave, a rising edge or a falling edge of a local peak or valley of a slow brain wave, a predefined sequence of at least one local temporal peak and at least one local temporal valley of a slow brain wave, or a rising or falling edge of such a sequence;

the supporting member comprises an adjustment device for adjusting to the diameter of the head of a person which enables changing a dimension of said supporting member according to a diameter of the head of a person;

the adjustment device of the supporting member is a soft flexible portion of the supporting member, in particular a portion of fabric or elastomer;

the adjustment device of the supporting member comprises at least two parts, rigid or semi-rigid, which are movable with respect to one another;

the supporting member is adapted to surround at least half a circumference of the head of the person P;

the device has a total weight of less than 200 grams.

The invention also relates to a method for stimulating slow brain waves of a person, in particular during a sleep period of said person, wherein the person wears a device according to one of claims 1 to 18, the supporting member of the device at least partially surrounding the head of said person so as to be held thereon, the method comprising, in soft real-time:

the capture of at least one measurement signal that represents a physiological electrical signal of the person, by means of the plurality of electrodes in contact with the skin of the person, the reception of said measurement signal by the embedded conditioning and control electronics, and the emission by the acoustic transducer, when so controlled by the embedded conditioning and control electronics, of an acoustic signal synchronized with a predefined slow brain wave temporal pattern.

According to one embodiment, the emission of an acoustic signal synchronized with a predefined slow brain wave temporal pattern comprises:

the determination, from the measurement signal, of a slow brain wave temporal waveform, the determination, from said slow brain wave temporal waveform, of at least one temporal moment of synchronization between the predefined slow brain wave temporal pattern and a predefined temporal pattern of the acoustic signal, and the controlling of the acoustic transducer so that the predefined temporal pattern of the acoustic signal is emitted at said temporal moment of synchronization.

In preferred embodiments of the invention, one or more of the following arrangements may possibly be used:

the determination, from the measurement signal, of a slow brain wave temporal waveform comprises adjusting an instantaneous phase of said temporal waveform according to an instantaneous phase of the measurement signal;

the determination, from the measurement signal, of a slow brain wave temporal waveform comprises:
  the determination of a temporal waveform oscillating at an average slow brain wave frequency of the person,
  the determination of an instantaneous phase difference between said temporal waveform and the measurement signal,
  the adjustment of an instantaneous phase of said temporal waveform according to an instantaneous phase of the measurement signal, based on said instantaneous phase difference;

the determination of an instantaneous phase difference between said temporal waveform and the measurement signal comprises the application of a low-pass filter to a product between the temporal waveform and the measurement signal;

the predefined slow brain wave temporal pattern has a predefined range of instantaneous phase values of the temporal waveform and/or a predefined range of absolute values of the measurement signal amplitude;

the temporal moment of synchronization is determined as being a temporal moment during which the instantaneous phase of the temporal waveform is within said predefined range of instantaneous phase values of the temporal waveform, if and only if the absolute value of the measurement signal amplitude has previously been within said predefined range of absolute values of the measurement signal amplitude;

a first temporal moment I1 is determined during which the absolute value of the measurement signal S amplitude is within the predefined range of absolute values of the measurement signal amplitude, a second temporal moment I2, subsequent to the first temporal moment I1, is determined during which the instantaneous phase of the temporal waveform F is within the predefined range of instantaneous phase values of the temporal waveform F, and if the first temporal moment I1 and the second temporal moment I2 are separated by a duration that is less than a predefined maximum duration, the moment of synchronization I is defined as the second temporal moment I2;

the average slow brain wave frequency of the person is determined from a measurement signal captured during a sleep period of said person that precedes the sleep period during which the method is implemented;

the average slow brain wave frequency of the person is determined dynamically, in particular, the average slow brain wave frequency of said person is determined dynamically from a portion of the measurement signal captured over a predefined duration preceding the moment at which the operation of determining the average slow brain wave frequency of the person is implemented;

the predefined temporal pattern M2 of the acoustic signal comprises a predefined number of intermittent signals, in particular less than five intermittent signals.

In one embodiment, the emission by the acoustic transducer, when so controlled by the embedded conditioning and control electronics, of an acoustic signal synchronized with a predefined slow brain wave temporal pattern is repeated at least once, in particular at least once during a sleep period of the person.

Through these arrangements, the invention can provide a device and a method for stimulating slow brain waves that is simple to use and accessible to non-medically trained personnel, that is compact and comfortable so that it can be used in an everyday context, which significantly enhances the beneficial effects of a person's sleep, which improves where appropriate the stability and duration of sleep stages, which is easily adaptable to the user so that it can be used by a variety of people without complex modifications, and which is simple and inexpensive to manufacture so as to guarantee its accessibility to the general public.

BRIEF DESCRIPTION OF DRAWINGS

Other features and advantages of the invention will be apparent from the following description of several of its embodiments, given by way of non-limiting examples, with reference to the accompanying drawings.

In the drawings.

In the various figures, the same references designate identical or similar elements.

MORE DETAILED DESCRIPTION

Figure 1:
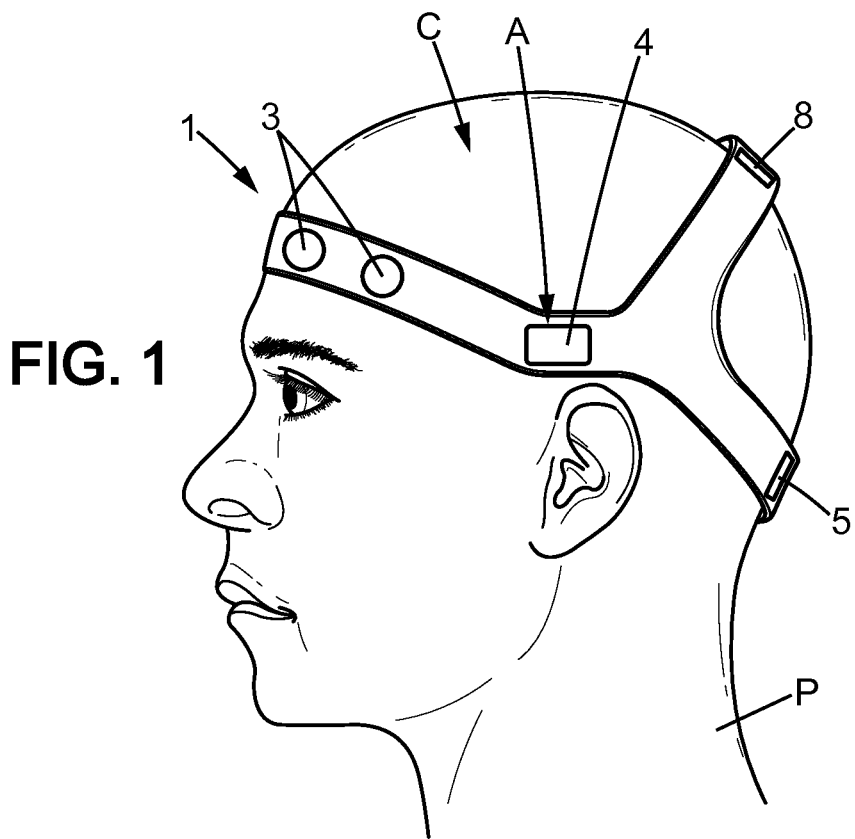
FIG. 1 is a schematic view of a self-contained device for stimulating slow wave brains that is worn on the head of a person, according to one embodiment of the invention.
Figure 2:
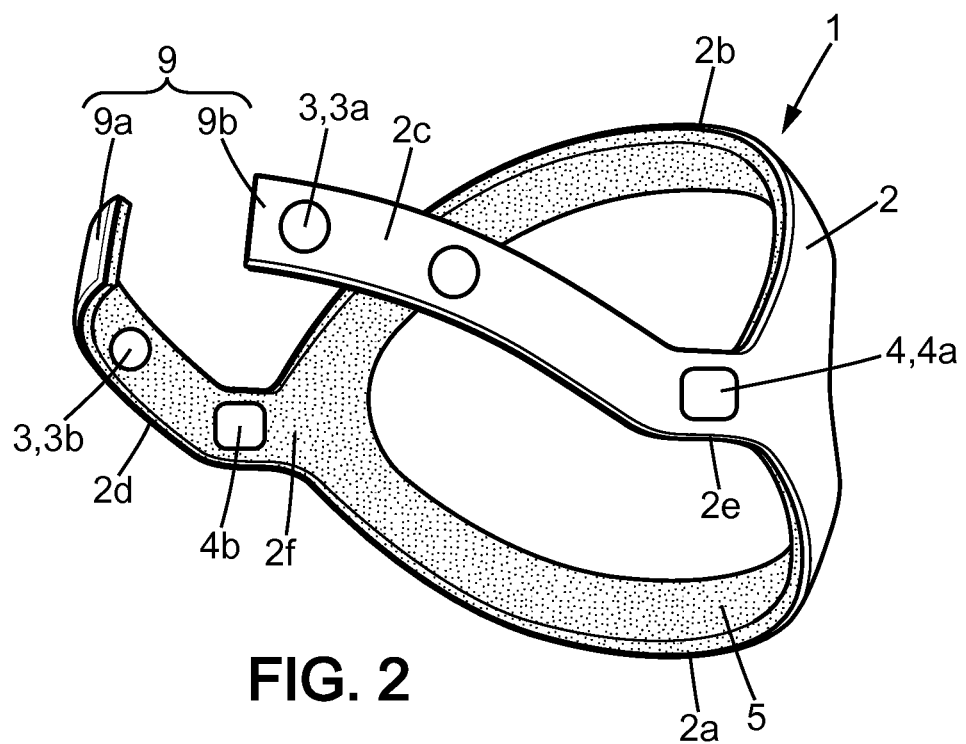
FIG. 2 is a detail perspective view of a self-contained device for stimulating slow brain waves according to one embodiment of the invention, where the device comprises in particular first and second acoustic transducers respectively adapted to emit acoustic signals respectively stimulating a right inner ear and a left inner ear of the person.

Referring firstly to FIGS. 1 and 2, the first object of the invention is a device 1 for stimulating slow brain waves.

The device 1 is adapted to be worn by a person P, in particular during the person's sleep period.

The device is adapted in particular to be worn on the head of the person P.

To this end, the device 1 comprises a supporting member 2. The supporting member 2 is adapted to surround the head of the person P at least partially so as to be held thereon. In one embodiment of the invention illustrated in FIG. 1, the supporting member 2 is particularly adapted to surround at least a portion of a circumference of the head of the person P, in particular surrounding at least half of a circumference of the head of the person P, or even entirely surrounding a diameter of the head of the person P.

In the embodiment illustrated in FIG. 1, the supporting member 2 has several arms 2a, 2b, 2c, 2d. The supporting member comprises in particular four arms interconnected at arm connection points 2e, 2f. The arms 2a, 2b, 2c, 2d surround different portions of the head of the person P so as to ensure stable retention and a precise positioning of the device 1 on the person P.

For example, a first arm 2a surrounds a back of the head, and a second arm 2b surrounds the top of the head. The first and second arms 2a, 2b are respectively connected at their respective ends at a left lateral arm connection point 2e and a right lateral arm connection point 2f, respectively located near the left and right temples of the person P. Finally, the third and fourth arms 2c, 2d respectively extend from the left lateral 2e and right lateral 2f arm connection points, towards the front of the person P.

The device 1 further comprises a plurality of electrodes 3, at least one acoustic transducer 4, and embedded conditioning and control electronics 5.

The electrodes 3, acoustic transducer 4, and electronics 5 are operatively connected to each other. Thus, the embedded conditioning and control electronics 5 are particularly suitable for controlling and for receiving information from the plurality of electrodes 3, and are also able to command and control the emission of an acoustic signal A by the acoustic transducer 4.

To this end, the electrodes 3, the acoustic transducer 4, and the electronics 5 are mounted on the supporting member 2. In this manner the electrodes 3, the acoustic transducer 4, and the electronics 5 are close to each other so that communication between these members 3, 4, 5 is particularly fast and high speed. In the example of FIG. 1, the electrodes are mounted on the third and fourth arms 2c, 2d, the electronics 5 are mounted on the first arm 2a, and two acoustic transducers 4 are respectively mounted near the left lateral 2e and right lateral 2f arm connection points. Of course, other arrangements of the components of the device 1 are possible.

This allows implementing an operation of stimulating the slow brain waves of a person P in soft real-time.

Thus, in particular, the electronics 5 are capable, in soft real-time, of receiving a measurement signal S from the plurality of electrodes 3 and controlling the emission by the acoustic transducer of an acoustic signal A synchronized with a predefined temporal pattern T of a slow brain wave of the person P.

"Synchronized with a predefined temporal pattern of a slow brain wave" is understood to mean that the acoustic signal emitted by the device is temporally synchronized with a slow brain wave of the person. More precisely, it means that the acoustic signal emitted by the device is temporally synchronized with an instantaneous phase of a slow brain wave of the person as detailed below.

"Soft real-time" is understood to mean an implementation of the stimulation operation such that the time constraints on this operation, in particular the duration of the operation or the frequency at which it is repeated, are satisfied on the average over a predefined total implementation duration, for example a few hours. It is understood that the implementation of said operation may at certain times exceed said time constraints as long as the average operation of the device 1 and the average implementation of the method satisfies these constraints over the predefined total implementation duration. Time limits may be predefined, beyond which the implementation of the stimulation operation is to be stopped or paused.

To enable such an implementation in soft real-time, a maximum distance between the electrodes 3, the acoustic transducer 4, and the electronics 5 may be less than approximately one meter and preferably less than a few decimeters. In this manner, sufficiently rapid communication between the elements of the device 1 can be guaranteed.

The electrodes 3, the acoustic transducer 4, and the electronics 5 may for example be housed in cavities of the supporting member 2, snapped onto the supporting member 2, or attached to the supporting member 2 for example by gluing, screwing, or other suitable means of attachment. In one embodiment of the invention, the electrodes 3, the acoustic transducer 4, and the electronics 5 may be detachably mounted on the supporting member 2.

Figure 3:
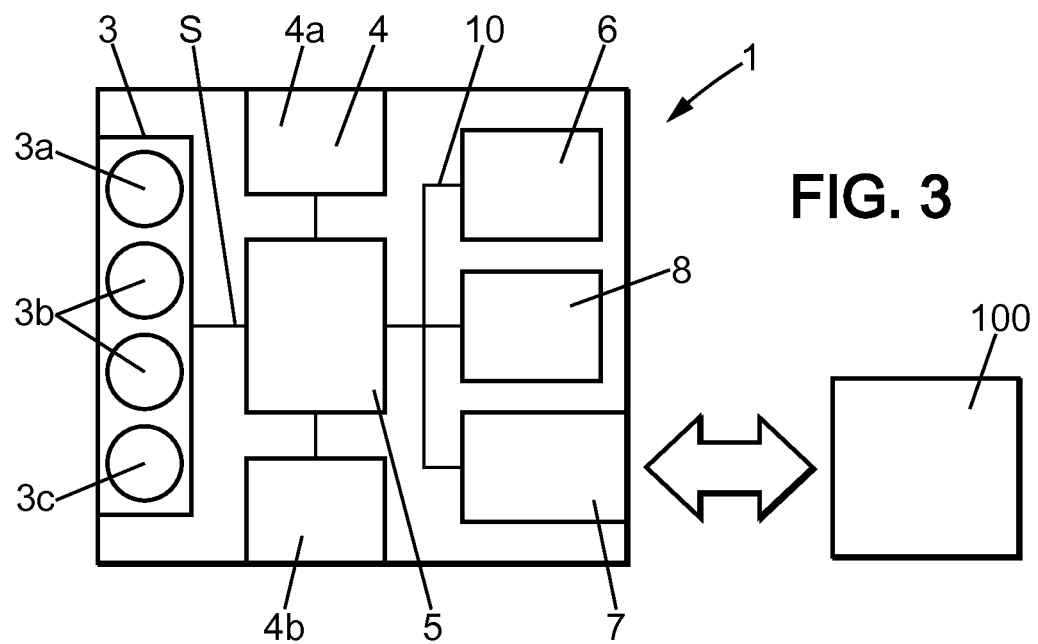
FIG. 3 is a block diagram of the device of FIG. 2, illustrating the elements of the device and the functional links between these elements.

Referring now to FIG. 3 as well, in one advantageous embodiment of the invention, the embedded conditioning and control electronics 5 are operatively connected to the electrodes 3 and to the acoustic transducer 4 by means of wire connections 10. In this manner, exposure of the person P to electromagnetic radiation is reduced.

The acoustic transducer 4 is adapted to emit an acoustic signal A stimulating at least one inner ear of the person P.

In a first embodiment illustrated in particular in FIGS. 1 and 2, the acoustic transducer 4 is an osteophonic device stimulating the inner ear of the person P by bone conduction.

This osteophonic device 4 may for example be adapted for placement near the ear, for example above it as illustrated in FIG. 1, in particular on a region of skin covering a cranial bone.

In a second embodiment, the acoustic transducer 4 is a speaker stimulating the inner ear of the person P via an ear canal leading to said inner ear.

This speaker may be placed outside the ear of the person P or in the ear canal.

The acoustic signal A is a modulated signal that at least partially lies within a frequency range audible to a person P, for example the range of 20 Hz to 30 kHz.

The electrodes 3 are adapted to be in contact with the person P, and in particular with the skin of the person P, in order to capture at least one measurement signal S representative of a physiologic electrical signal E of the person P.

The physiological electrical signal E may in particular be an electroencephalogram (EEG), electro-myogram (EMG), electrooculogram (EOG), electrocardiogram (ECG), or any other biosignal measurable in a person P.

In particular, the physiological electrical signal E advantageously is an electroencephalogram (EEG) of the person P.

To this end, in one embodiment of the invention, the device 1 comprises at least two electrodes 3 of which at least one is a reference electrode 3a and at least one is an EEG measurement electrode 3b.

The device 1 may further comprise a ground electrode 3c.

In one particular embodiment, the device 1 comprises at least three EEG measurement electrodes 3c, so as to capture physiological electrical signals E comprising at least three electroencephalogram measurement channels.

The EEG measurement electrodes 3c are for example arranged on the surface of the scalp of the person P.

In other embodiments, the device 1 may further comprise an EMG measurement electrode, and possibly an EOG measurement electrode.

The measurement electrodes 3 may be reusable electrodes or disposable electrodes. Advantageously, the measurement electrodes 3 are reusable electrodes in order to simplify the everyday use of the device.

The measurement electrodes 3 may be dry electrodes or electrodes coated with contact gel. The electrodes 3 may also be textile or silicone electrodes.

In one embodiment of the invention, the measurement electrodes 3 are active electrodes adapted to preprocess the measurement signal S, for example to perform at least one of the following preprocessing operations:

frequency filtering, for example frequency filtering of the measurement signal S within a range of temporal frequencies of interest, for example a frequency range within 0.3 Hz to 100 Hz, amplification, for example amplification of the measurement signal S by a factor ranging from $10^3$ to $10^6$, and/or sampling the measurement signal S by means of an analog-to-digital converter adapted, for example, to sample the measurement signal S at a sampling rate of several hundred Hertz, for example 256 Hz or 512 Hz.

Such preprocessing of the measurement signal S may for example be implemented by an analog module of the measurement electrode 3 or by an analog module located near the measurement electrode 3.

The embedded conditioning and control electronics 5 receive the measurement signals S from the electrodes 3, possibly preprocessed as detailed above.

If the measurement signals S received by the electronics 5 are not preprocessed, the electronics 5 may apply one and/or more preprocessing operations as detailed above.

The embedded conditioning electronics 5 include one or more microchips, for example at least one microprocessor.

As detailed above, the embedded conditioning and control electronics 5 are adapted to implement an operation of stimulating slow brain waves of the person P, an operation which will now be described in more detail.

"Slow brain wave" is understood to mean an electrical brain wave of the person P having a frequency that is less than 5 Hz and greater than 0.3 Hz. "Slow brain wave" can be understood to mean an electrical brain wave of the person P that has a peak-to-peak amplitude of for example between 10 and 200 microvolts.

Aside from very low frequency waves of less than 1 Hz, a slow brain wave thus is also understood to mean the higher frequency delta waves (usually between 1.6 and 4 Hz). A slow brain wave can also be understood to mean any type of wave having the frequency and amplitude characteristics mentioned above. For example, stage 2 sleep waves referred to as "K-complexes" can be considered slow brain waves for the invention.

It is thus understood that implementation of the operation of stimulating slow brain waves according to the invention may not be limited to a deep sleep stage of the person P (commonly called stage 3 or stage 4) but may also be performed during other sleep stages, such as during light sleep (usually called stage 2).

It should be noted, however, that such slow brain waves are usually not observed in phases of ("paradoxical sleep" (or REM sleep)), in particular the dream phases.

In general, implementation of the invention may not be limited to a particular sleep stage of the person P (as identified by example in the AASM standards, acronym for "American Academy of Sleep Medicine").

Figure 5:
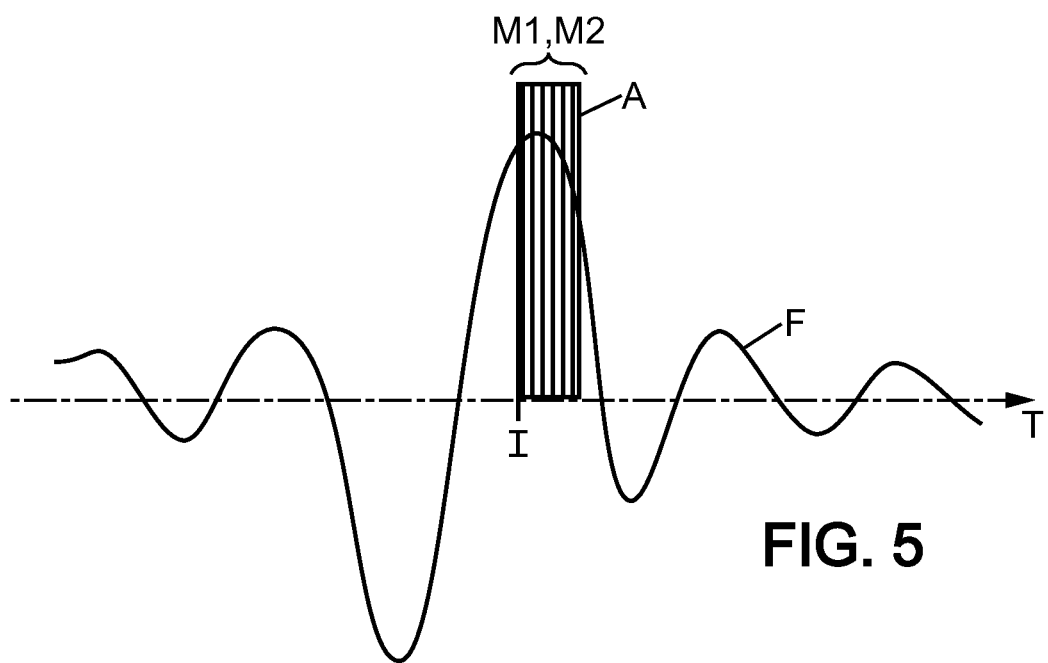
FIG. 5 illustrates a temporal waveform of a slow brain wave, an acoustic signal, and predefined temporal patterns according to an exemplary embodiment of the invention.

To implement the slow brain wave stimulation operation, the electronics 5 are for example adapted for determining, from the measurement signal S, firstly a temporal waveform F of a slow brain wave C such as the one illustrated in FIG. 5.

In a first embodiment, the temporal waveform F is a series of sampled points of amplitude values of the measurement signal S, possibly preprocessed as mentioned above, said series of measurement points possibly being interpolated or resampled.

In a second embodiment, the temporal waveform F is a series of amplitude values generated by a phase-locked loop (commonly referred to as the acronym PLL). The phase-locked loop is such that the instantaneous phase of the temporal waveform F that is output from said loop is adjusted according to the instantaneous phase of the measurement signal S.

The phase-locked loop may be implemented by analog means or digital means, for example in a programmable digital chip or an analog electronic component.

As detailed hereinafter, said phase-locked loop may comprise means for determining a difference in instantaneous phase between the temporal waveform F and the measurement signal S. Said means may also be implemented by analog means or digital means, for example in a programmable digital chip or an analog electronic component.

In one embodiment of the invention, the temporal waveform F can thus be determined by a phase-locked loop (also called a phase lock loop).

The phase-locked loop may be such that the instantaneous phase of the temporal waveform F is adjusted according to the instantaneous phase of the measurement signal S.

An average frequency w of a slow brain wave of the person P may be determined by analysis of the brain waves of the person P.

In a first embodiment, the average frequency w of slow brain waves of the person P may be determined in a prior analysis step of the waves.

The prior analysis step of the brain waves of the person P may for example include analysis of the measurement signal S captured during a preceding sleep period in order to determine an average frequency of the slow brain waves of the person P.

To determine the average frequency of the slow brain waves, a time or frequency filter can be applied to the measurement signal S captured during a preceding sleep period, in particular so as to retain only the measurement signal associated with a sleep period of interest, for example a period of deep sleep, and/or to remove measurement artifacts or too high frequencies.

Next, an average frequency of the slow brain waves can be extracted from said filtered measurement signal.

In a second embodiment, the average frequency w of the slow brain waves of the person P can be determined dynamically during implementation of the method.

To do so, one can analyze a portion of the measurement signal S captured over a predefined duration preceding the moment when the operation of determining the average slow brain wave frequency of the person is performed. The measurement signal S may for example be stored in a buffer for this purpose.

Such a predefined duration may for example range from a few tens of seconds to a few minutes.

Prior to said analysis, filtering operations may also be applied to said portion of the measurement signal as detailed above.

Analysis of said portion of the measurement signal S allows extracting an average frequency of the slow brain waves from said portion of the measurement signal.

Once the average frequency w of the slow brain waves of the person P is determined, a temporal waveform F can be generated at said average frequency w of the slow brain waves.

The measurement signal S, possibly filtered beforehand, can be normalized, for example between −1 and 1.

An instantaneous phase difference D between the temporal waveform F and the measurement signal S can then be determined, for example as follows.

Assuming that the measurement signal S and the temporal waveform F have the following simplified forms:

$$S = \cos(wt+\varphi) \qquad (1)$$

$$F = \cos(wt+\psi) \qquad (2)$$

where $\varphi$ is an instantaneous phase of the measurement signal S, $\psi$ is an instantaneous phase of the temporal waveform F, and w is the average frequency of the brain wave C.

An instantaneous phase difference D between the temporal form F and the measurement signal S can then be determined as follows:

$$D = LP[\cos(wt+\varphi)\cos(wt+\psi)] \simeq \sin\varphi-\psi \simeq \varphi-\psi \qquad (3)$$

where LP is a low-pass function.

The temporal waveform F can then be controlled based on the instantaneous phase difference D, in order to synchronize the instantaneous phase of the temporal waveform F and the instantaneous phase of the measurement signal S.

Thus, in the example of equations (1) to (3) given above, we seek to minimize the instantaneous phase difference D in order to synchronize the temporal waveform F and the measurement signal S.

To do so, the temporal waveform F can be shifted in time or phase, for example by directly adjusting the instantaneous phase $\psi$ of the temporal waveform F, so as to minimize the phase signal. The information (absolute or relative) on the amplitude of the measurement signal S can be reassociated with the temporal waveform F so as to obtain a representation of the instantaneous phase and of the measurement signal amplitude.

It is therefore understood in general that the temporal waveform F is a representation of the brain wave C that can directly correspond to the measurement signal S and/or can be obtained by a phase-locked loop on the basis of the measurement signal S.

Generating the temporal waveform F using a phase-locked loop allows obtaining a cleaner signal.

In particular, the instantaneous phase of the temporal waveform F and of the brain wave C are temporally synchronized.

In the present description, where appropriate, "brain wave C" is understood to mean the values of the temporal waveform F.

From this temporal waveform F, the electronics 5 are capable of determining at least one temporal moment I of synchronization between a predefined temporal pattern M1 of a slow brain wave C and a predefined temporal pattern M2 of the acoustic signal A.

Next, the electronics 5 are adapted to control the acoustic transducer 4 so that the predefined temporal pattern M2 of the acoustic signal A is emitted at the temporal moment I of synchronization.

The predefined temporal pattern M1 of the slow brain wave C is therefore a pattern of amplitude values and/or phase values of the temporal waveform F that represents the slow brain wave C and/or the measurement signal S.

Pattern of amplitude values and/or phase values is understood to mean a temporal sequence of amplitude values and/or phase values, possibly associated with predefined temporal moments (in other words, a curve of amplitude values and/or phase values). More simply, it also means an amplitude value and/or a phase value or a range of amplitude values and/or phase values.

The temporal moment of synchronization I can thus be determined when the amplitude and/or phase of the temporal waveform F which represents the slow brain wave C and/or of the measurement signal S is equal to the amplitude values and/or phase values of the predefined temporal pattern M1.

In particular, the predefined temporal pattern M1 can be a sequence of phase values of the temporal waveform F and can therefore be independent of the absolute value of the amplitude of the temporal waveform F.

For example, the predefined temporal pattern M1 may be a predefined range of instantaneous phase values of the temporal waveform F.

Such a predefined range of instantaneous phase values of the temporal waveform F will be for example an instantaneous phase ψ between pi and 3/2*pi radians, corresponding to a rising edge of the brain wave C for the temporal waveform F of equation (2) given above (F=cos(wt+ψ)). The predefined temporal pattern M1 can also be a sequence of relative values of the amplitude of the temporal waveform F. Said relative values are for example relative to a maximum amplitude of the temporal waveform F, predefined or stored.

In one embodiment of the invention, the predefined temporal pattern M1 may thus for example correspond to a local temporal peak of the slow brain wave C, a local temporal valley of the slow brain wave C, or a predefined sequence of at least one local temporal peak and at least one local temporal valley of the slow brain wave C. The predefined temporal pattern M1 may also correspond to a portion of such a peak, valley, or of such a sequence, for example a rising edge, a falling edge, or a plateau.

The predefined temporal pattern M1 may further be a function of absolute values of the amplitude of the temporal waveform F, for example a range of absolute values of the amplitude of the temporal waveform F, particularly when the temporal waveform F retains information concerning the amplitude of the measurement signal S.

By way of non-limiting example, the predefined temporal pattern M1 may correspond to absolute values of the amplitude of the temporal waveform F that are below a predefined stimulation triggering threshold, for example absolute values of the amplitude below −30 millivolts (in this case it is therefore a range limited at one end).

The predefined temporal pattern M1 may comprise several of the different embodiments described above.

When the predefined temporal pattern M1 has several ranges of values, the temporal moment of synchronization I can be determined when said ranges of values are checked simultaneously or sequentially.

For example, the predefined temporal pattern M1 may comprise a predefined range of instantaneous phase values of the temporal waveform F and a predefined range of absolute values of the amplitude of the measurement signal contained in the temporal waveform F.

The predefined range of instantaneous phase values is for example the instantaneous phases between pi and 3/2*pi radians.

The predefined range of amplitude absolute values is for example the amplitude absolute values less than −30 millivolts.

In a first embodiment, the temporal moment of synchronization I can be determined as being a moment when the values of the temporal waveform F simultaneously satisfy said ranges of instantaneous phase values and of absolute amplitude values.

In a second embodiment, the temporal moment of synchronization I can be determined as being a temporal moment when the instantaneous phase of the temporal waveform F is within the predefined range of instantaneous phase values of the temporal waveform F, if and only if the absolute value of the measurement signal S amplitude was previously within the predefined range of absolute values of the measurement signal amplitude.

The maximum duration between the respective presence of said instantaneous phase and amplitude absolute value within said respective ranges may be predefined, to limit false pattern detections.

More specifically, the absolute value of the measurement signal S amplitude may be within the predefined range of absolute values of the measurement signal amplitude at a first temporal moment I1. The instantaneous phase of the temporal waveform F may be within the predefined range of instantaneous phase values of the temporal waveform F at a second temporal moment I2, subsequent to the first temporal moment I1.

If the first and second moments I1 and I2 are separated by a duration that is less than said predefined maximum duration, the temporal moment of synchronization I can then be defined as the second temporal moment I2.

Similarly, the predefined temporal pattern M2 of the acoustic signal may be a pattern of amplitude values and/or phase values of the acoustic signal A.

In a first embodiment, the acoustic signal is for example an intermittent signal as illustrated in FIG. 5. This intermittent signal is emitted for example for a duration that is less than a period of a slow brain wave. The duration of the intermittent signal is for example less than a few seconds, more preferably less than one second. In an example given for purely indicative and non-limiting purposes, the acoustic signal A is for example a pink noise pulse of type 1/f, of a temporal duration of 50 to 100 milliseconds with a rise time and fall time of a few milliseconds. Still non-limiting and for clarification purposes, in this example the predefined temporal pattern M1 of the slow brain wave C may for example correspond to a rising edge of a local peak of the slow brain wave C. The predefined temporal pattern M2 of the acoustic signal A can then be for example a rising edge of the pink noise pulse. In this example, the temporal moment of synchronization I between the predefined temporal pattern M1 of the slow brain wave C and the predefined temporal pattern M2 of the acoustic signal A may for example be defined so that the rising edge of the pink noise pulse A and the rising edge of the local peak of the slow brain wave C are synchronized, meaning concurrent.

The predefined temporal pattern M2 of the acoustic signal may include a predefined number of intermittent signals, in particular less than five intermittent signals, for example two or three pink noise pulses.

In another embodiment, the acoustic signal A may be a continuous signal. The duration of the acoustic signal A may then be greater than a period of the slow brain wave C. "Continuous signal" is understood to mean a signal of long duration compared to a period of the slow brain wave C.

In this embodiment, the acoustic signal A may be temporally modulated in amplitude, frequency, or phase, and the predefined temporal pattern M2 of the acoustic signal A may then be such a temporal modulation.

Alternatively, the continuous acoustic signal A may not be temporally modulated, for example in a manner which will now be described.

The device 1 may comprise at least two acoustic transducers 4, in particular a first acoustic transducer 4a and a second acoustic transducer 4b as shown in FIG. 2. The first acoustic transducer 4a is adapted to emit an acoustic signal A1 stimulating a right inner ear of the person P. The second acoustic transducer 4b is adapted to emit an acoustic signal A2 stimulating a left inner ear of the person P.

One can then in particular control the first and second acoustic transducers 4a, 4b so that the acoustic signals A1 and A2 are binaural acoustic signals A. To this end, the acoustic signals A1 and A2 may for example be continuous signals of different frequencies.

Such acoustic signals A1, A2 are known to generate intermittent pulses in the brain of the person P, called binaural beats.

Still for non-limiting and clarification purposes, in this example the predefined temporal pattern M1 of the slow brain wave C may, for example, again correspond to a rising edge of a local peak of the slow brain wave C. The predefined temporal patterns M2 of the acoustic signals A1, A2 may be ranges of the acoustic signals A1, A2 temporally corresponding to said intermittent pulses generated in the brain of the person P. In this example, the temporal moment of synchronization I between the predefined temporal pattern M1 of the slow brain wave C and the predefined temporal patterns M2 of the acoustic signals A1, A2 may for example be defined such that an intermittent pulse generated in the brain of the person P is temporally synchronized with the rising edge of the local peak of the slow brain wave C.

Depending on the embodiments and depending on the temporal pattern M1 selected, different embodiments are possible for determining the temporal moment of synchronization I.

FIG. 5 illustrates an example of predefined temporal patterns M1 and M2.

To determine temporal moment I, the electronics 5 may for example compare the amplitude values of the measurement signal S, possibly filtered and/or normalized, to an amplitude threshold.

In the example given above in a purely non-limiting manner, the predefined temporal pattern M1 of the slow brain wave C corresponds to a rising edge of a local peak of the slow brain wave C. A temporal moment I then corresponds to a temporal moment where the amplitude threshold is exceeded, or to a predefined duration immediately following such an exceeding moment. The electronics 5 can thus control the acoustic transducer 4 so that the predefined temporal pattern M2 of the acoustic signal A is temporally synchronized with said temporal moment I.

It is understood that the speed of communication between the electrodes 3, the acoustic transducer 4, and the electronics 5 ensures reliable synchronization and optimal implementation of the stimulation operation.

In one embodiment where the temporal waveform F is a series of amplitude values generated by a phase-locked loop, it is possible to determine said temporal moment I from said phase-locked loop, by threshold detection or by predicting the future values of the temporal waveform F.

In this embodiment, the temporal waveform F may be less noisy than the measurement signal S and facilitate determination of the temporal moment of synchronization I. In this manner, it is easier to use the phase values of the temporal waveform F to identify temporal moment I.

In all embodiments, it is possible to implement an operation of reinforcement learning to refine the parameters for determining temporal moment I, for example the amplitude thresholds, the shape of the predefined temporal pattern M1, or the parameters of the phase-locked loop. Such a reinforcement learning operation is particularly indicated in the measurement of physiological electrical signals which are highly variable from one person P to another.

The parameters of the stimulation operation, and in particular of the sub-operation of determining temporal moment I, can thus be adjusted during implementation of the stimulation operation or during implementation of successive stimulation operations, for example to adjust said parameters to the person P.

As detailed above, the embedded conditioning and control electronics 5 comprise means for determining a slow brain wave temporal waveform F, determining at least one temporal moment of synchronization between the predefined slow brain wave temporal pattern (M1), and controlling the acoustic transducer 4.

Said means of the embedded conditioning and control electronics 5 are for example microchips, microprocessors, and/or electronic memories, mounted and interconnected as appropriate on flexible or rigid printed circuit boards and operatively connected to the electrodes 3 and to the transducer 4 via wired connections 10.

The device 1 may further comprise a memory 6 as illustrated in FIG. 3. The memory 6 is adapted to be mounted on the supporting member 2, for example as described above for the electrodes 3, the acoustic transducer 4, and the electronics 5. The memory 6 may be permanently mounted on the supporting member 2 or may be a removable module, for example a memory card such as an SD card (acronym for "Secure Digital").

The memory 6 may be operatively connected to the electronics 5. The memory 6 may be controlled by the embedded conditioning and control electronics 5 so as to store the measurement signals S.

In one advantageous embodiment of the invention, the memory 6 is capable of storing measurement signals S for a duration of several hours, for example at least eight hours so as to cover an average sleep period of a person P.

The device 1 may further comprise a communication module 7 for communicating with an external server 100. The communication module 7 may be mounted on the supporting member 2 as described above for the electrodes 3, the acoustic transducer 4, and electronics 5. The communication module 7 may be controlled by the embedded conditioning and control electronics 5.

The electronics 5 may in particular be adapted to control the communication module 7 to transfer the measurement signals S stored in memory 6 to the external server 100. The transfer operation may be implemented after a sleep period of the person P.

The communication module 7 may advantageously be a wireless communication module, for example a module implementing a protocol such as Bluetooth or Wi-Fi.

In this manner, when the P person is in a sleep period, he or she is not disturbed by cables, in particular if it is necessary to transmit data during the sleep period.

The device 1 may also comprise a battery 8. The battery 8 may be mounted on the supporting member 2 as described above for the electrodes 3, the acoustic transducer 4, and the electronics 5. The battery 8 may be capable of supplying power to the plurality of electrodes 3, the acoustic transducer 4, and the electronics 5, and where appropriate the memory 6 and the communication module 7. The battery 8 is preferably adapted to supply power for several hours without recharging, more preferably for at least eight hours so as to cover an average sleep period of a person P.

The device 1 can thus operate autonomously during a sleep period of the person P. In this manner in particular, the device 1 is self-contained and adapted to implement one or more operations of stimulating slow brain waves without communicating with an external server 100, in particular without communicating with an external server 100 for several minutes, more preferably several hours, more preferably at least eight hours. This reduces the exposure of the person P to electromagnetic radiation.

"Self-contained" is thus understood to mean that the device can operate for an extended period of several minutes, preferably several hours, in particular at least eight hours, without needing to be recharged with electrical energy, communicate with external elements such as an external server, or be structurally connected to an external device such as a securing member such as an arm or a bracket.

In this manner the device is suitable for use in the everyday life of a person P without imposing particular constraints.

Furthermore, the supporting member 2 advantageously comprises a device 9 for adjusting to the diameter of the head of the person P. This allows adjusting device 1 to the person P and therefore enables particularly good contact between the electrodes 3 and the skin of the person P.

The adjustment device 9 allows changing a dimension of the supporting member 2 according to a diameter of the head of a person P, to allow fine-tuned adjustment to said diameter.

In one embodiment illustrated in particular in FIG. 1, the adjustment device 9 comprises at least two parts 9a, 9b that are movable with respect to one another. The parts 9a, 9b may be rigid or semi-rigid. In the example of FIG. 1, the parts 9a and 9b are respectively the ends of the third and fourth arms 2c, 2d of the supporting member 2. In this embodiment, the supporting member 2 and parts 9a and 9b are sufficiently rigid for the parts 9a and 9b to tend to approach one another. In this manner, the device 1 can be adjusted to and remain in place on the head of the person P.

In a variant of this embodiment, the adjustment device 9 may also include a lock adapted to prevent or allow a relative movement of said two parts 9a, 9b. The lock may be an integral part of one of parts 9a, 9b or may be an element independent of the two parts 9a, 9b.

In another embodiment of the invention, the adjustment device 9 is a soft and flexible portion of the supporting member 2. This portion may be a portion of fabric or elastomer, for example of stretch fabric.

Advantageously, the device 1 may be adapted to be worn by the person P without effort for a period of several hours. For this purpose it may have a reduced weight, for example a total weight of less than 200 grams.

Figure 4:
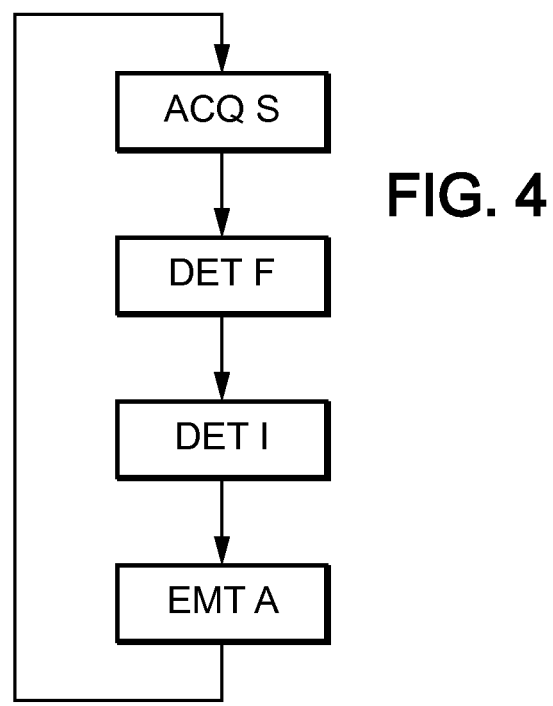
FIG. 4 is a flowchart illustrating one embodiment of a method for stimulating slow brain waves according to an embodiment of the invention.

Referring to FIG. 4, the invention also relates to a method for stimulating slow brain waves of a person P. This method is particularly suitable for implementation during a sleep period of the person P.

In this method, the person P wears a device 1 as described above. The supporting member 2 of the device 1 at least partially surrounds the head of the person P so as to be held in place thereon. The electrodes 3 are thus in contact with the skin of the person P, so as to be able to capture physiological electrical signals of the person P. The electrodes 3 are for example arranged close to the brain of the person P in order to capture an encephalogram of the person P.

The method then comprises an operation of stimulating a slow brain wave, comprising the following sub-operations:

capture of at least one measurement signal S that represents a physiological electrical signal of the person P, by means of the plurality of electrodes 3 in contact with the skin of the person P, reception of said measurement signal S by the embedded conditioning and control electronics 5, and emission by the acoustic transducer 4, when so controlled by the embedded conditioning and control electronics 5, of an acoustic signal A synchronized with a predefined temporal pattern M1 of a slow brain wave C.

These sub-operations are implemented in soft real-time as detailed above.

Thus, in particular, the emission of an acoustic signal A synchronized with the predefined temporal pattern M1 of a slow brain wave comprises:

determination, from the measurement signal S, of a slow brain wave temporal waveform F, determination, from said slow brain wave temporal waveform F, of at least one temporal moment of synchronization I between the predefined slow brain wave temporal pattern M1 and a predefined temporal pattern M2 of the acoustic signal A, and controlling of the acoustic transducer 4 so that the predefined temporal pattern M2 of the acoustic signal A is emitted at said temporal moment of synchronization I.

In one advantageous embodiment of the invention, the sub-operation of the emission by the acoustic transducer 4, when so controlled by the electronics 5, of an acoustic signal A synchronized with the predefined temporal pattern M1 of the slow brain wave C is repeated at least once. This sub-operation may be repeated several times during a sleep period of the person.

In one exemplary embodiment, the entire operation of stimulating slow brain waves is repeated at least once, and preferably several times, in particular during a sleep period of the person P.

The invention claimed is:

1. A device, configured to be worn by a person, for stimulating slow brain waves, the device comprising:

a supporting member, configured to partially surround a head of a person so as to be held thereon, the supporting member having mounted thereon:

a plurality of electrodes, configured to be in contact with the person to capture one measurement signal representative of a physiological electrical signal of said person, one acoustic transducer that emits an acoustic signal stimulating an inner ear of said person, and embedded conditioning and control electronics that, in soft real-time, receive the measurement signal from the plurality of electrodes and control the emission by the acoustic transducer of the acoustic signal synchronized with a predefined slow brain wave temporal pattern, wherein said embedded conditioning and control electronics are configured to, in soft real-time and with the supporting member of the device partially surrounding the head of the person:

capture the one measurement signal representative of the physiological electrical signal of the person, by means of the plurality of electrodes in contact with skin of the person;

receive said measurement signal by the embedded conditioning and control electronics; and emit, via the acoustic transducer controlled by the embedded conditioning and control electronics, the acoustic signal synchronized with the predefined slow brain wave temporal pattern, wherein the embedded conditioning and control electronics, for emitting the acoustic signal via the acoustic transducer, are configured to:

determine, from the measurement signal, a slow brain wave temporal waveform, determine, from said slow brain wave temporal waveform, one temporal moment of synchronization between the predefined slow brain wave temporal pattern and a predefined temporal pattern of the acoustic signal, and control the acoustic transducer to emit the predefined temporal pattern of the acoustic signal at said temporal moment of synchronization, and wherein, for determining said slow brain wave temporal waveform from said measurement signal, the embedded conditioning and control electronics are configured to:

determine a temporal waveform oscillating at an average slow brain wave frequency of the person, determine an instantaneous phase difference between said temporal waveform and the measurement signal, and adjust an instantaneous phase of said temporal waveform according to an instantaneous phase of the measurement signal, based on said instantaneous phase difference.

2. The device according to claim 1, wherein the embedded conditioning and control electronics comprise a phase-locked loop for determining the slow brain wave temporal waveform.

3. The device according to claim 2, wherein the phase-locked loop adjusts an instantaneous phase of the temporal waveform according to an instantaneous phase of the measurement signal.

4. The device according to claim 2, wherein the phase-locked loop comprises means for determining an instantaneous phase difference between the temporal waveform and the measurement signal.

5. The device according to claim 1, wherein the predefined slow brain wave temporal pattern has a predefined range of instantaneous phase values of the temporal waveform and/or a predefined range of absolute values of the measurement signal amplitude.

6. The device according to claim 1, wherein the acoustic transducer is a speaker that stimulates the inner ear of the person via an ear canal, or an osteophonic device that stimulates the inner ear of the person via bone conduction.

7. The device according to claim 1, further comprising: wired connections, and wherein the embedded conditioning and control electronics receive the measurement signal from the plurality of electrodes and control the acoustic transducer by means of the wired connections.

8. The device according to claim 1, further comprising: a memory mounted on the supporting member, controlled by the embedded conditioning and control electronics and configured to store the measurement signals.

9. The device according to claim 8, wherein the memory is configured to store an average slow brain wave frequency of the person.

10. The device according to claim 8, further comprising: a module for communicating with an external server, mounted on the supporting member, controlled by the embedded conditioning and control electronics, and configured to transfer the stored measurement signals to the external server.

11. The device according to claim 1, wherein the device is self-contained and implements a slow brain wave stimulation operation without communicating with an external server.

12. The device according to claim 1, further comprising: a battery mounted on the supporting member, the battery configured to supply power to the plurality of electrodes, the acoustic transducer, and the embedded conditioning and control electronics.

13. The device according to claim 1, wherein the slow brain wave has a frequency less than 5 Hz and greater than 0.3 Hz.

14. The device according to claim 1,
wherein the acoustic signal is an intermittent signal, and
wherein a duration of the acoustic signal is less than a period of a slow brain wave.

15. The device according to claim 1,
wherein the acoustic signal is a continuous signal, and
wherein a duration of the acoustic signal is greater than a period of a slow brain wave.

16. The device according to claim 15, further comprising: a second acoustic transducer,
said acoustic transducer and said second acoustic transducer configured to emit respective acoustic signals for respectively stimulating a right inner ear and a left inner ear of the person, the acoustic signals emitted by said acoustic transducer and said second acoustic transducer being binaural acoustic signals.

17. The device according to claim 1, wherein the predefined slow brain wave temporal pattern corresponds to a local temporal peak of a slow brain wave, a local temporal valley of a slow wave brain, a rising edge or a falling edge of a local peak or valley of a slow brain wave, a predefined sequence of one local temporal peak and one local temporal valley of a slow brain wave, or a rising or falling edge of such a sequence.

18. The device according to claim 1, wherein the supporting member comprises an adjustment device for adjusting to the diameter of the head of the person, said adjustment device configured to permit changing of a dimension of said supporting member in accordance with a diameter of the head of the person.

19. The device according to claim 18, wherein the adjustment device of the supporting member is a soft flexible portion of the supporting member.

20. The device according to claim 18, wherein the adjustment device of the supporting member comprises two parts that are rigid or semi-rigid, and that are movable with respect to one another.

21. The device according to claim 1, wherein the supporting member is configured to surround half a circumference of the head of the person.

22. The device according to claim 1, wherein the device has a total weight of less than 200 grams.

23. A method for stimulating slow brain waves of a person, wherein the person wears a device for stimulating slow brain waves and that is configured to be worn by the person, the device being comprised of a supporting member configured to partially surround the head of the person so as to be held thereon, and the device having mounted thereon:
a plurality of electrodes configured to be in contact with the person to capture one measurement signal that represents a physiological electrical signal of the person,
one acoustic transducer that emits an acoustic signal stimulating an inner ear of the person, and
embedded conditioning and control electronics that, in soft real-time, receives the measurement signal from the plurality of electrodes and controls the emission by the acoustic transducer of said acoustic signal synchronized with a predefined slow brain wave temporal pattern, the method comprising, in soft real-time and with the supporting member of the device partially surrounding the head of the person:
capturing the one measurement signal that represents the physiological electrical signal of the person, by means of the plurality of electrodes in contact with skin of the person;
receiving said measurement signal by the embedded conditioning and control electronics; and emitting, by the acoustic transducer, when so controlled by the embedded conditioning and
control electronics, the acoustic signal synchronized with the predefined slow brain wave temporal pattern,
wherein the emitting of the acoustic signal synchronized with the predefined slow brain wave temporal pattern includes steps carried out by the embedded conditioning and control electronics of:
determination of a slow brain wave temporal waveform from the measurement signal,
determination, from said slow brain wave temporal waveform, of one temporal moment of synchronization between the predefined slow brain wave temporal pattern and a predefined temporal pattern of the acoustic signal, and
controlling of the acoustic transducer to emit the predefined temporal pattern of the acoustic signal at said temporal moment of synchronization, and
wherein the determination of said slow brain wave temporal waveform comprises:
determination of a temporal waveform oscillating at an average slow brain wave frequency of the person,
determination of an instantaneous phase difference between said temporal waveform and the measurement signal, and
adjustment of an instantaneous phase of said temporal waveform according to an instantaneous phase of the measurement signal, based on said instantaneous phase difference.

24. The method according to claim 23, wherein the determination of the instantaneous phase difference between said temporal waveform and the measurement signal comprises application of a low-pass filter to a product between the temporal waveform and the measurement signal.

25. The method according to claim 23, wherein the predefined slow brain wave temporal pattern has a predefined range of instantaneous phase values of the temporal waveform and/or a predefined range of absolute values of the measurement signal amplitude.

26. The method according to claim 25, wherein the temporal moment of synchronization is determined as being a temporal moment during which the instantaneous phase of the temporal waveform is within said predefined range of instantaneous phase values of the temporal waveform, if and only if an absolute value of the measurement signal amplitude has previously been within said predefined range of absolute values of the measurement signal amplitude.

27. The method according to claim 26, wherein:
a first temporal moment is determined during which the absolute value of the measurement signal amplitude is within the predefined range of absolute values of the measurement signal amplitude,
a second temporal moment, subsequent to the first temporal moment, is determined during which the instantaneous phase of the temporal waveform is within the predefined range of instantaneous phase values of the temporal waveform, and
if the first temporal moment and the second temporal moment are separated by a duration that is less than a predefined maximum duration, the moment of synchronization is defined as the second temporal moment.

28. The method according to claim 23, wherein the average slow brain wave frequency of the person is determined from a measurement signal captured during a sleep period of the person that precedes the sleep period during which the method is implemented.

29. The method according to claim 23, wherein the average slow brain wave frequency of the person is determined dynamically.

30. The method according to claim 23, wherein the predefined temporal pattern of the acoustic signal comprises a predefined number of intermittent signals.

31. The method according to claim 23, wherein the emitting by the acoustic transducer, when so controlled by the embedded conditioning and control electronics, of the acoustic signal synchronized with the predefined slow brain wave temporal pattern is repeated at least once.

* * * * *